United States Patent
Fernández Molina et al.

(10) Patent No.: US 12,280,109 B2
(45) Date of Patent: *Apr. 22, 2025

(54) NANO-PARTICLES THAT CONTAIN SYNTHETIC VARIANTS OF GM3 GANGLIOSIDE AS ADJUVANTS IN VACCINES

(71) Applicant: Centro de Inmunología Molecular, Havana (CU)

(72) Inventors: Luis Enrique Fernández Molina, Havana (CU); Belinda Sánchez Ramírez, Havana (CU); Audry Fernández Gómez, Havana (CU); Gretchen Bergado Báez, Havana (CU); Circe Mesa Pardillo, Havana (CU); Lisset Chao García, Sancti Spiritus (CU); Narjara González Suárez, Havana (CU); Dayana Pérez Martínez, Havana (CU); Diana Rosa Hernández Fernández, Havana (CU); Mabel Cruz Rodríguez, Havana (CU); Ángel Alexis Manso Vargas, Havana (CU); Vicente Guillermo Verez Bencomo, Havana (CU); Blanca Idelmis Tolón Murguía, Havana (CU); Miguel Antonio López López, Havana (CU); Jesús Arturo Junco Barranco, Camagüey (CU)

(73) Assignee: Centro de Inmunología Molecular, Havana (CU)

( * ) Notice: Subject to any disclaimer, the term of this patent is extended or adjusted under 35 U.S.C. 154(b) by 0 days.

This patent is subject to a terminal disclaimer.

(21) Appl. No.: 18/375,788

(22) Filed: Oct. 2, 2023

(65) Prior Publication Data
US 2024/0131152 A1    Apr. 25, 2024

Related U.S. Application Data

(63) Continuation of application No. 16/760,954, filed as application No. PCT/CU2018/050003 on Oct. 24, 2018, now Pat. No. 11,806,396.

(30) Foreign Application Priority Data
Nov. 6, 2017    (CU) .................................. 2017-0137

(51) Int. Cl.
*A61K 39/39*    (2006.01)
*A61K 9/51*    (2006.01)
(Continued)

(52) U.S. Cl.
CPC ............ *A61K 39/39* (2013.01); *A61K 9/5161* (2013.01); *A61K 9/5169* (2013.01);
(Continued)

(58) Field of Classification Search
CPC ....................................................... A61K 39/39
See application file for complete search history.

(56) References Cited

U.S. PATENT DOCUMENTS 6,149,921 A * 11/2000 Rodriguez ..... A61K 39/001171
530/387.5
7,776,346 B2    8/2010 O'Connor et al.
(Continued)

FOREIGN PATENT DOCUMENTS

EP    1356822 A2    10/2003
EP    2335736 A1    6/2011
(Continued)

OTHER PUBLICATIONS

Mansi Saxena, Sjoerd H. van der Burg, Cornelis J. M. Melief, and Nina Bhardwaj. "Therapeutic cancer vaccines." Nature Reviews, vol. 21, Jun. 2021, pp. 360-378. (Year: 2021).*
(Continued)

*Primary Examiner* — Isaac Shomer
(74) *Attorney, Agent, or Firm* — Foley Hoag LLP; Philip S. Choi; Erin Foley (57) ABSTRACT

This invention describes ways of obtaining nano-particulated adjuvants formed by different synthetic variants of
(Continued)

GM3 ganglioside. Depending on the fine structure of the fatty acid in the ceramide of the synthetic GM3, said adjuvants are able to stimulate specifically and in a specialized way the humoral or cellular immune response against accompanying antigens. Particularly, this invention provides immunogenic vaccine compositions that comprise peptides, polypeptides or proteins and the aforementioned nanoparticles, which are formed through the dispersion of hydrophobic proteins of the outer membrane complex (OMC) of *Neisseria meningitidis* in solutions containing fully synthetic variants of the GM3 ganglioside.

24 Claims, 6 Drawing Sheets

Specification includes a Sequence Listing.

(51) Int. Cl.
    *A61K 39/00* (2006.01)
    *A61P 35/00* (2006.01)
(52) U.S. Cl.
    CPC .............. *A61K 39/001106* (2018.08); *A61K 39/001144* (2018.08); *A61P 35/00* (2018.01); *A61K 2039/55516* (2013.01); *A61K 2039/55555* (2013.01); *A61K 2039/55572* (2013.01)

(56) References Cited

U.S. PATENT DOCUMENTS

| | | | |
|---|---|---|---|
| 11,806,396 B2* | 11/2023 | Fernandez Molina | A61P 35/00 |
| 2002/0136735 A1 | 9/2002 | Molina et al. | |
| 2007/0148181 A1* | 6/2007 | Molina | A61K 39/39 514/54 |
| 2011/0250196 A1 | 10/2011 | Junco Barranco et al. | |
| 2014/0127301 A1* | 5/2014 | Alexis | A61P 19/02 424/85.4 |
| 2016/0166667 A1 | 6/2016 | Sánchez Ramírez et al. | |
| 2020/0268878 A1 | 8/2020 | Molina et al. | |

FOREIGN PATENT DOCUMENTS

| | | |
|---|---|---|
| EP | 3028714 A1 | 6/2016 |
| WO | WO-2019/086056 A1 | 5/2019 |

OTHER PUBLICATIONS

Matti Sallberg, Malin Weiland, and Lars Frelin. "Therapeutic vaccines: challenges of chronic viral infections." Drug Discovery Today: Therapeutic Strategies, vol. 4 No. 4, 2007, pp. 253-266. (Year: 2007).*

Li Yang, Claire M Edwards, and Gregory R Mundy. "Gr-1+ CD11b+ Myeloid-Derived Suppressor Cells: Formidable Partners in Tumor Metastasis." Journal of Bone and Mineral Research, vol. 25, No. 8, Aug. 2010, pp. 1701-1706. (Year: 2010).*

Jeong Hyun Lee et al. "Long-primed germinal centres with enduring affinity maturation and clonal migration." Nature, vol. 609, Sep. 22, 2022, pp. 998-1004 and 20 additional unnumbered pages. (Year: 2022).*

Junhua Zhu, Yu-Teh Li, Su-Chen Li and Richard B.Cole. "Structural characterization of gangliosides isolated from mullet milt using electrospray ionization-tandem mass spectrometry." Glycobiology, vol. 9, No. 10, 1999, pp. 985-993. (Year: 1999).*

Ana M. Bada Barro et al. "Non-clinical immuno-toxicological evaluation of HER1 cancer vaccine in non-human primates: a 12-month study." Vaccine, vol. 31, 2012, pp. 89-95. (Year: 2012).*

A. Marabelle, L. Tselikas, T. de Baere, and R. Houot. "Intratumoral immunotherapy: using the tumor as the remedy." Annals of Oncology, vol. 28 (Supplement 12), 2017, pp. xii33-xii43. (Year: 2017).*

Alving et al., "Liposomal adjuvants for human vaccines," Expert Opinion on Drug Delivery, 13(6): pp. 807-816 (2016).

Arteaga et al., "Evaluation and evidence of natural gangliosides with two unsaturated bonds in the ceramide structure obtained by a combination of MALDI-MS and NMR spectroscopy", Anal Bioanal Chem (2011) 400: 3675-3680.

Barro et al., "Non-clinical immuno-toxicological evaluation of HER1 cancer vaccine in non-human primates: a 12-month study", *Vaccine* 31(1): 89-95 (2012).

Branca., "Rekindling cancer vaccines," Nature Biotechnology, 34(10): 1019-1024 (2016).

Editorial., "The problem with neoantigen prediction," Nature Biotechnology, 35(2): 97 (2017).

Estevez et al., "Enhancement of the immune response to poorly immunogenic gangliosides after incorporation into very small size proteoliposomes (VSSP)," Vaccine, 18: 190-197 (2000).

Fernández et al., "Very small size proteoliposomes abrogate cross-presentation of tumor antigens by myeloid-derived suppressor cells and induce their differentiation to dendritic cells", *Journal for Immuno Therapy of Cancer* 2: 1-16 (2014).

Garrido et al., "Evaluation and evidence of natural gangliosides with two unsaturated bonds in the ceramide structure obtained by a combination of MALDI-MS and NMR spectroscopy," *Analytical and bioanalytical chemistry* 400: 3675-3680 (2011).

International Search Report and Written Opinion for International Application No. PCT/CU2018/050003 dated Apr. 1, 2019.

Jinshu et al., "A synthetic gonadotropin-releasing hormone (GnRH) vaccine for control of fertility and hormone dependent diseases without any adjuvant," Vaccine, 23(4): 4834-4843 (2005).

Junco et al., "Immunotherapy of prostate cancer in a murine model using a novel GnRH based vaccine candidate," Vaccine, 25: 8460-8468 (2007).

Khong et al., "Adjuvants for peptide-based cancer vaccines," Journal for Immuno Therapy of Cancer, 4: Article 56 (2016).

Labrada Mon et al., "Direct validation of NGcGM3 ganglioside as a new target for cancer immunotherapy", Expert Opin. Biol. Ther. 2010, vol. 10, No. 2, pp. 153-162.

Labrada Mon, "Mecanismos inmunológicos asociados a la vacunación terapéutica de cáncer con NGcGM3/VSSP." Anales de la Academia de Ciencias de Cuba (2016).

Lee et al., "Long-primed germinal centres with enduring affinity maturation and clonal migration", Nature 609.7929: 998-1004 (2022).

Lee et al., "Rapid profiling of bovine and human milk gangliosides by matrix-assisted laser desorption/ionization Fourier transform ion cyclotron resonance mass spectrometry," International Journal of Mass Spectrometry, 305: 138-150 (2011).

Mauri et al., "A procedure for the preparation of GM3 ganglioside from GM1-lactone," Glycoconjugate Journal, 16: 197-203 (1999).

Mazorra et al., "Immunization with a GM3 ganglioside nanoparticulated vaccine confers an effector CD8+ T cells-mediated protection against melanoma B16 challenge," Cancer Immunology, Immunotherapy, 57(12): 1771-1780 (2008).

Silhavy et al., "The bacterial cell envelope", *Cold Spring Harbor perspectives in biology* 2.5: a000414 (2010).

Tran et al., "Final common pathway' of human cancer immunotherapy: targeting random somatic mutations," Nature Immunology, 18(3): 255-262 (2017).

Wilkerson et al., "Nanoparticle systems modulating myeloid-derived suppressor cells for cancer immunotherapy", *Current Topics in Medicinal Chemistry* 17.16: 1843-1857 (2017).

Xu et al., "Lipid-Mediated Targeting with Membrane-Wrapped Nanoparticles in the Presence of Corona Formation," ACS Nano, 10(1): 1189-1200 (2016).

Yang et al., "Gr−1+CD11b+ Myeloid-Derived Suppressor Cells: Formidable Partners in Tumor Metastasis," Journal of Bone and Mineral Research 25(8): pp. 1701-1706 (2010).

Yu et al., "Dressing up nanoparticles: A membrane wrap to induce formation of the virological synapse", *Acs Nano* 9.4: 4182-4192 (2015).

(56) References Cited

OTHER PUBLICATIONS

Zhu et al., "Structural characterization of gangliosides isolated from mullet milt using electrospray ionization-tandem mass spectrometry", Glycobiology 9(10): 985-993 (1999).

* cited by examiner

| Vaccine | Animals without tumor (overall animals) | Rate (%) |
|---|---|---|
| *Control* | 7(7) | 0 |
| *OVA/VSSP nat* | 2(10) | 20 |
| *OVA/VSSP ole* | 5(10) | 50 | p = 0,012

NANO-PARTICLES THAT CONTAIN SYNTHETIC VARIANTS OF GM3 GANGLIOSIDE AS ADJUVANTS IN VACCINES

CROSS-REFERENCE TO RELATED APPLICATIONS

This application is a Continuation of application Ser. No. 16/760,954, filed on May 1, 2020, now U.S. Pat. No. 11,806,396, issued on Nov. 7, 2023, which is the U.S. national phase of International Patent Application No. PCT/CU2018/050003, filed on Oct. 24, 2018, which claims the benefit of priority to Cuban Patent Application Serial No. CU 2017-0137, filed on Nov. 6, 2017; the entire contents of each of said applications are incorporated herein in their entirety by this reference.

SEQUENCE LISTING

A Sequence Listing in the form of an XML file (entitled "IAC-00102_SL.xml", created on Nov. 18, 2024, and having a size of 4, 179 bytes) is hereby incorporated by reference in its entirety.

FIELD OF THE TECHNIQUE

The present invention relates to the fields of immuno-nanotechnology and immuno-oncology, especially to therapeutic vaccines for the treatment of individuals with cancer and/or chronic infections caused by oncogenic viruses. Particularly it describes nano-particulate adjuvants specialized in specifically stimulating the cellular or humoral immune effectors in these patients and provides the corresponding vaccine compositions.

BACKGROUND

After decades of unsuccessful results in clinical trials, therapeutic cancer vaccines have failed to become an effective and low toxicity treatment with benefit for patients. Recent clinical successes obtained with immune checkpoint inhibitors antibodies (Abs) have stimulated commercial and scientific interest in immuno-oncology, including cancer vaccines. The failures of these therapeutic vaccines may have been due to factors such as an incorrect selection of the antigens, the use of relatively inefficient vehicles/adjuvants and the use of said vaccines as monotherapy, that is, not in combination with other immunomodulators that allow for the correction of the negative effect exerted by the tumor microenvironment (Branca M A et al (2016) Nat Biotech 34 (10): 1019-24). Traditionally, cancer vaccines have used in their formulation proteins classified as self-associated tumor antigens, which although they are aberrantly expressed in tumor cells, are also present in normal tissues. The lack of solid evidence of the effectiveness in the clinic of these vaccines may be due in part to the central tolerance process by means of which the elimination of T cells that have receptors with high avidity against most of these antigens occurs (Tran E. et al (2017) Nat Immunol 18 (3): 255-62). Therefore, the success of cancer vaccines based on this type of antigens will depend on the use of novel specialized adjuvants capable of potentiating a specific response of effector T cells, which is relatively weak at the beginning, but afterwards increases in such a way that the tumor becomes a source of natural neo-antigens. This allows to mobilize a powerful multispecific and personalized action of cytotoxic T lymphocytes (CTL), capable of eradicating malignant lesions.

Recently the state of the art reflects a change of perspective regarding to the selection of antigens for successful cancer vaccines with the introduction of tumor neo-antigens. An attractive source of these neo-antigens is the personalized detection of individual tumor mutations. Another more limited source of this type of antigen comes from the sequences of viral oncogenic proteins. Although these mutated peptides would have the advantage of being new to the immune system (they are not present in normal tissues) and are therefore more immunogenic, the success of the new vaccines designed with these neo-antigens would also depend on the capacity of novel adjuvants of maximizing the CTL responses, seeking an optimal availability of the antigen through a local persistence that allows its presentation by antigen-presenting cells (APC) in a context of successful maturation and additionally circumvent the immunosuppressive effect of the tumor microenvironment (TME). On the other hand, the identification of true neo-epitopes in practice is an ineffective procedure. Sequencing studies identify thousands of somatic mutations in individual tumors and bioinformatics programs predict hundreds of mutated peptides capable of binding to specific MHC but the vast majority of these neo-epitopes are not found in real tumors when they are isolated and studied by mass spectrometry, and even worse, only a few are able to stimulate an CTL response. This means that the current methodology of prediction and validation of neo-epitopes is far from being routinely used to bring personalized immunotherapy to clinical practice (Editorial, (2017) Nat Biotech 35 (2): 97).

For all types of vaccines the selection of the appropriate adjuvant is a crucial element to achieve the desired success. The main objective of a therapeutic cancer vaccine is to stimulate the activation and proliferation of B lymphocytes, T cells and mediators of innate immunity in such a way that the induced humoral and cellular immune effectors are able of recognize and destroy tumor cells, thus increasing the survival and quality of life of patients. In order to achieve this purpose an ideal adjuvant must first optimize the availability of antigens for the APCs. Secondly, it must effectively stimulate these APCs so that they express the necessary co-stimulatory signals and secrete specific cytokines and chemokines. Thirdly, it must be able to modulate the TME in such a way that the immunosuppressive effects are neutralized. Nowadays, an adjuvant with all these characteristics are not available.

As explained by Khong H. et al. (Khong H. et al (2016) J. Immunother. Cancer 4:56), among most promising variants of adjuvants for cancer vaccines in the art are micro and nanoparticles because they can exhibit several desired properties as vaccination enhancers. These particulate preparations can be designed to enable the accompanying antigen to effectively target specific APCs, by means of the regulation of particle sizes, stiffness and net charge. Particulate vaccines with diameters in the range of 500-2000 nm are preferentially captured by APC at the injection site and moved to the lymph nodes (LN), while particles from 20 to 200 nm passively drain to the LN where they are captured by the resident APCs. The most used micro and nanoparticles for these purposes are liposomes, proteoliposomes, synthetic polymers and natural polymers. The advantages and limitations of each of these nanoparticles have been described in detail in the art.

Particularly pertinent for this invention is the description by Xu F. et al. (Xu F. et al (2016) ACS Nano Vol. 10:1189-

1200) of a synthetic nano-particulate adjuvant that contains GM3 ganglioside in its composition. This adjuvant was obtained by coating gold nano-particles of diameters from 40 to 80 nm with a lipid membrane in which the GM3 ganglioside was inserted. In this way, the glycolipid-receptor specific interaction principle can be advantageously addressed, particularly the interaction of sialyl-lactose with Siglec1 (CD169), which is over-expressed in activated dendritic cells (DC), protagonists of the synapse with CD4+ T cells in the LNs. Although these nanoparticles coated with GM3 are accumulated selectively in vivo in the CD169$^+$ DCs of popliteal LNs, there is no evidence from immunization experiments with reference antigens of their potential as adjuvant or of their efficacy in tumor models. On the other hand, this principle is only functional in nano-particles with diameters ranging from 40 to 80 nm Molina et al. in U.S. Pat. No. 7,776,346 describe ways to prepare effective immunogens by associating very small size proteoliposomes (VSSP), formed by the hydrophobic conjugation of the outer membrane protein complex (OMPC) of the *Neisseria meningitidis* bacterium with the ganglioside GM3, to certain poorly immunogenic antigens, which can be considered as the closest technical solution to the present invention. Also, the way to obtain these VSSPs has been described in some detail by Rodríguez et al. in U.S. Pat. No. 6,149,921, emphasizing that the GM3 ganglioside used to obtain these proteoliposomes must be obtained from biological sources, mainly from the mass of hybridomas resulting from the industrial production of monoclonal Abs. Estévez et al. (Estévez et al (2000) Vaccine Vol. 18:90-197), teach that these VSSP can also be produced using GM3 obtained from canine erythrocytes. It is known in the art, as explained by Lee H et al. (Lee H et al (2011) Int J Mass Spectr Vol 305: 138-150) that the GM3 ganglioside obtained from any natural source is composed by a variable mixture of different molecular species where the structure of the oligosaccharide is the same but that of the ceramide varies in terms of fatty acid composition. Apart from the inconvenience of using components of animal or tumor origin to produce pharmaceutical preparations, the use of GM3 of biological origin largely prevents obtaining VSSP with the necessary highly reproducible characteristics. It should be established that before being described in the present invention no previous technical solution or scientific publication describes VSSP variants obtained by manufacturing process employing different fully synthetic GM3 with chemically defined structures. These synthetic variants also has the surprising property of functioning as specialized adjuvants for therapeutic vaccines, depending on the molecular fine structure of the GM3 ganglioside used in its preparation and that this specialization provides new adjuvants with advantageous properties, compared to VSSP produced with GM3 from biological sources. Therefore, the novelty of this invention consists in providing new VSSP nano-particulated adjuvants containing fully synthetic GM3 ganglioside, basically but not restricted to the structures of GM3 with ceramides containing either stearic acid, GM3 (18:0), primarily for the induction of potent antibody responses against accompanying antigens or oleic acid, GM3 (18:1), particularly effective in the induction of specific CTL effector responses.

BRIEF DESCRIPTION OF THE INVENTION

In an embodiment of the present invention, we describe adjuvants comprising nanoparticles formed by the association of fully synthetic variants of GM3 ganglioside with hydrophobic proteins of the outer membrane complex of the bacterium *N. meningitidis*, basically but not restricted to compositions having in the ceramide of the GM3 ganglioside stearic acid or oleic acid.

In another embodiment, the present invention relates to peptides, polypeptides or proteins vaccine compositions comprising the aforementioned nano-particulated adjuvants, and optionally another adjuvant that can be but is not limited to alum or an oily adjuvant. Particularly, the antigens in these vaccine compositions are the extracellular domains of growth factor receptors or portions thereof such as HER1, HER2 or HER3 alone or in combination; or the peptide PyrGnRHm1-TT, related to the GnRH hormone. Said vaccine compositions can be used in the manufacture of a medicament for the treatment of cancer or chronic viral infections with oncogenic viruses.

In a particular embodiment, the present invention relates to the use of vaccine compositions comprising the nano-particulated adjuvants object of the present invention, either alone or in combination, in the stimulation of the antigen specific humoral or cellular immune response of a patient.

Additionally, it is also object of the present invention a method of treatment for administering to a subject in need of such treatment the vaccine compositions of the present invention subcutaneously (SC), intradermally, intramuscularly, intranodally intratumorally or by direct application on mucous membranes, with a fortnightly frequency during at least a total of five induction doses and subsequently in monthly maintenance doses for at least six months. Said compositions can be administered simultaneously, staggered or alternately.

DETAILED DESCRIPTION OF THE INVENTION

Vaccine Compositions

The vaccine compositions used in the present invention are formed by the association of a nano-particulated adjuvant, formed by the dispersion of hydrophobic proteins from the OMPC of *N. meningitidis* in solutions of fully synthetic variants of the GM3 ganglioside, to peptides, polypeptides or proteins as antigens. Particularly these peptides, polypeptides or proteins can be the full extracellular domains of growth factor receptors or portions thereof and also related to hormones associated in certain stages with tumor progression, such as GnRH, without being limited to them.

The type of fatty acid present in the ceramide of GM3 ganglioside, included in one of the VSSPs of the present invention will depend on the purpose of the vaccine; in case that the desired effect is to favor an Abs response, stearic acid (GM3 18:0) will be used, whereas if it is to favor CTL response, oleic acid (GM3 18:1) will be used. It is also possible to induce in the host a dual response of Abs and CTL against the same antigen by adequately combining immunizations with both vaccine formulations. Both the VSSP containing GM3 (18:0) and those that have GM3 (18:1) can be used alone or combined with other adjuvants such as but not limited to alum or oily formulations.

The vaccine compositions of the present invention that use VSSP with GM3 (18:0) as an adjuvant, compared to vaccine formulations adjuvated with the nanoparticles containing the ganglioside obtained from a natural source, have a superior quality in terms of the induced humoral response, the serological recognition of tumor cell lines, the serological inhibition of receptor activation in tumor cells as well as a decrease in the viability of these cells.

The vaccine compositions of the present invention that use VSSP with GM3 (18:1) as an adjuvant, compared to vaccine formulations adjuvated with the nanoparticles containing the ganglioside obtained from a natural source, induce a more potent CTL response.

Therapeutic Application and Treatment Methods

The present invention provides vaccine compositions specialized in inducing Abs or CTL responses, against a family of growth factor receptors, which constitutes a particularly useful solution for this antigenic system of interest in Immuno-Oncology, since it is known that both Abs response and specific CTL responses are effective but difficult to optimize in a single vaccine formulation and with a single administration scheme.

It is also the purpose of this invention to introduce vaccine formulations specialized in generating high titers of neutralizing Abs against hormones associated in certain stages, with tumor progression, particularly but not limited to GnRH hormone.

Another object of the present invention is to provide therapeutic vaccine compositions capable of generating powerful specific responses of Abs or CTL, especially in immunocompromised patients suffering from cancer or chronic viral infections with oncogenic viruses.

The vaccine compositions of the present invention can be administered to the patient by: SC, intradermal, intramuscular, intranodal, intratumoral routes or by direct application on mucous membranes.

Among the types of cancer that can be treated with the vaccine compositions object of the present invention are carcinomas of epithelial origin. More particularly, examples of these cancers include lung cancer (small cell and non-small cell types), hepatocellular cancer, gastric cancer, pancreatic cancer, head and neck cancer, glioblastoma, cervical cancer, ovarian cancer, bladder cancer, breast cancer, colorectal cancer, prostate cancer, salivary gland carcinoma, kidney cancer, vulva and thyroid tumors, anal carcinoma and penile carcinoma.

The range of doses to be used in humans of the extracellular domains of the growth factor receptors or portions thereof in the vaccine compositions of the present invention is between 200 µg to 1 mg, preferably within the range from 400 µg to 900 µg. The range of doses to be used of the GnRH peptide in the vaccine compositions of the present invention is between 500 µg to 3 mg, preferably within the range from 1 mg to 2.5 mg. The VSSPs are administered in a range between 100 µg and 1 mg, preferably from 200 µg to 600 µg (according to OMPC content).

Said compositions are administered to the subjects with a fortnightly frequency during at least a total of five doses of induction and subsequently in monthly maintenance doses for at least six months. If the desired effect is to induce in the host a dual response of Abs and CTL against the same antigen, the immunizations can be combined with both vaccine formulations simultaneously, staggered or alternately.

Obtaining of the Nano-Particulated Adjuvant VSSP GM3 (18:0)

First, the OMPC of *N. meningitidis* is dispersed in a Tris-HCL buffer solution containing a mixture of sodium deoxycholate (10-40 mM) and sodium dodecyl sulfate (1-10 mM) in a reactor and stirred for a time period ranging from 1 to 36 hours. Next, a mass of the synthetic ganglioside (GM3 18:0) from 0.1 to 3 times the added mass of OMPC is added and the stirring is prolonged. Subsequently, the detergents are removed by ultrafiltration or dialysis. The ultrafiltered remnant solution is concentrated to adjust its concentration to the desired dosage which is from 0.1 to 1 mg/ml of OMPC and sterilized by filtration in a sterile 0.2 µm pore size capsule.

Obtaining of the Nano-Particulated Adjuvant VSSP GM3 (18:1)

First, the OMPC of *N. meningitidis* is dispersed in a Tris-HCL buffer solution containing a mixture of sodium deoxycholate (10-40 mM) and sodium dodecyl sulfate (1-10 mM) in a reactor and is stirred for a time period ranging from 1 to 36 hours. Next, a mass of the synthetic ganglioside (GM3 18:1) from 0.1 to 3 times the added mass of OMPC is added and agitation is prolonged. Subsequently, the detergents are removed by ultrafiltration or dialysis. The ultrafiltered remnant solution is concentrated to adjust its concentration to the desired dosage which is from 0.1 to 1 mg/ml of OMPC and is sterilized by filtration in a sterile capsule of 0.2 µm pore size.

Preparation of the HER1, HER1+HER2 and HER3 Vaccine Compositions with VSSP GM3 (18:0) as Adjuvant The preferred vaccine compositions in this invention that contain HER1 or HER1+HER2 or HER3 as growth factor receptors and VSSP GM3 (18:0) as adjuvant, for the induction of a potent specific humoral immune response are prepared as follows: the contents of the individual vials of HER1 or HER1+HER2 or HER3 antigen in solution or freeze-dried, and the VSSP GM3 18:0 solution, stored previously between 4 and 20° C., are mixed separately for 10-30 minutes next to the patient's bed before injecting it, so that the final proportion of the mass of antigen and that of the VSSP GM3 (18:0) (according to OMPC content) is in the range from 300 µg to 2 mg.

Preparation of the HER1, HER1+HER2 and HER3 Vaccine Compositions with VSSP GM3 (18:1) as Adjuvant The preferred vaccine compositions of this invention that contain HER1 or HER1+HER2 or HER3 as growth factors receptors and VSSP GM3 (18:1) as an adjuvant, for the induction of potent specific cellular immune responses are prepared as follows: the content of the individual vials of the HER1, HER1+HER2 or HER3 antigen, in solution or lyophilized, and VSSP GM3 (18:1) solution, stored at temperature range from 4 to 20° C., are mixed separately for 10-30 minutes next to the bedside of the patient before injecting it, so that the final proportion of the mass of the antigen and that of VSSP GM3 (18:1) (according to OMPC content) is in the range from 300 µg to 2 mg.

Preparation of GnRHm1-TT Peptide Vaccine Compositions with VSSP GM3 (18:0) as Adjuvant The GnRHm1-TT peptide was prepared by substituting in the biosynthetic process the amino acid L-Glycine of the sixth position that it normally occupies in the sequence of natural GnRH (EHWSYGLRPG) (SEQ ID NO: 1), by an L-Proline (EHWSYPLRPG) (SEQ ID NO: 2). To complete its construction, the QYIKANSKFIGITEL (SEQ ID NO: 3) epitope of tetanus toxoid (Junco J A et al (2007) Vaccine 25:8460-68) was added during the process of synthesis, following the solid phase method (Hougten et al., (1986) Biotechniques 4:522-6); the peptide thus prepared for the purpose of the present invention will be hereinafter referred to as PyrGnRHm1-TT.

The preferred vaccine compositions in this invention that contain the PyrGnRHm1-TT and VSSP GM3 (18:0) as adjuvant, for the induction of a potent specific humoral immune response can be prepared as follows: the content of the Individual vials of PyrGnRHm1-TT antigen in solution or lyophilized, and VSSP 18:0, stored previously at a temperature range from 4 to 20° C., are mixed separately for 10-30 minutes at the bedside of the patient before the injection, in such a way that that the final proportion of the mass of the antigen and that of VSSP GM3 (18:0) (according to OMPC content) is within the range from 600 μg to 4 mg.

EXAMPLES

Figure 1:
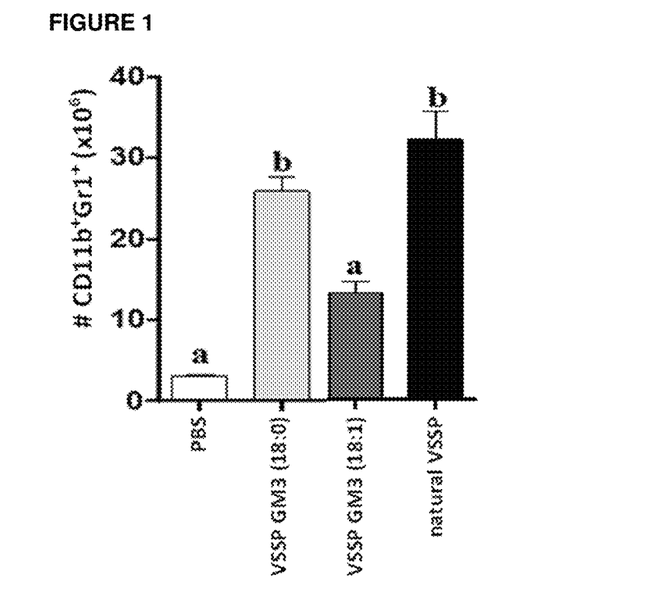
FIG. 1. Accumulation of $CD11b^+GR1^+$ cells in the spleen of mice carrying the MCA203 tumor and treated with VSSP nanoparticles containing different GM3 molecular species, measured by flow cytometry.

Example 1. The Administration of VSSP GM3 (18:1) in Mice Bearing the MCA203 Tumor does not Increase the Number of CD11b+GR1+ Cells in the Spleen Four groups of female C57BL/6 mice (3 animals per group) were inoculated by SC route on day 0 with $1 \times 10^6$ cells of MCA203. Subsequently, on days 11, 12 and 18, the VSSP GM3 (natural source), the VSSP GM3 (18:1) and the VSSP GM3 (18:0) (200 μg of OMPC) were injected by SC route, to the mice of three of the groups, the fourth group of mice was left as untreated control and a phosphate buffer was administered to it. On day 22, the animals were sacrificed and the extracted spleens were analyzed individually by flow cytometry to determine the number of $CD11b^+Gr1^+$ cells. Animals treated with VSSP GM3 (18:1) (FIG. 1) showed similar quantity of these regulatory cells if compared with tumor bearing mice just receiving buffer. On the other hand $CD11b^+Gr1^+$ cells significantly increased in the spleens of the animals injected with VSSP GM3 (natural source) and VSSP GM3 (18:0) (equal letters p>0.05, different letters p<0.05, ANOVA and Tukey tests).

Example 2. Vaccination with OVA/VSSP GM3 (18:1) Induces Three Times More Specific Cytotoxicity of T CD8+ Cells, as Compared to OVA/VSSP GM3 (Natural Source) and OVA/VS3 GM3 (18:0)

Figure 2:
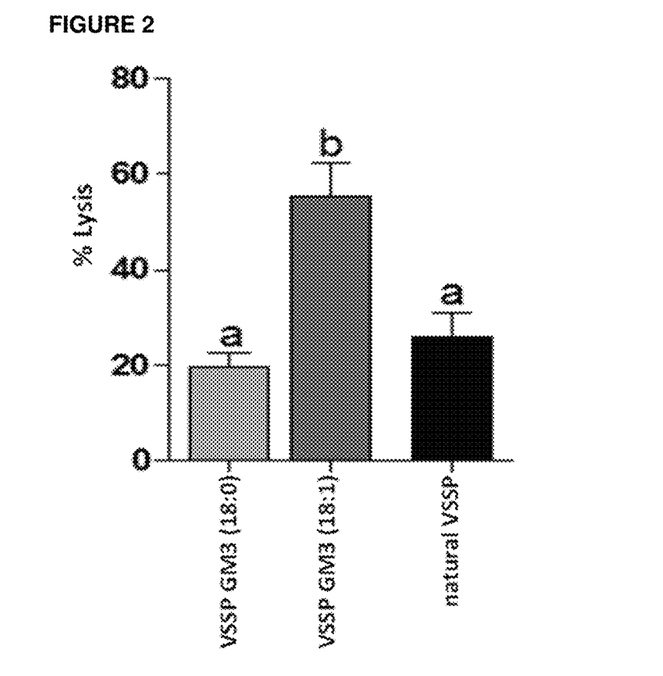
FIG. 2. Measurement by flow cytometry of the in vivo antigen-specific CTL response induced in mice immunized with OVA/VSSP GM3 (18:1), OVA/VSSP GM3 (18:0) and OVA/VSSP GM3 (natural source).

The in vivo CTL antigen-specific response was compared in female C57BL/6 mice (3 animals per group) immunized with three different formulations of the OVA antigen: one using VSSP GM3 (natural source) nano-particles, other with VSSP GM3 (18:1) and a third one using VSSP GM3 (18:0) as adjuvants. The vaccines were administered SC on days 0, 1 and 7 (200 μg OMPC). In parallel splenocytes were obtained from naive animals that were differentially labeled with CFSE (5 min at 37° C.). Highly labelled cells (5 μM) were used as target cells after incubation with the SIINFEKL peptide (1 μM, 90 min at 37° C. and 5% $CO_2$), while lower labelled cells (0.33 μM) without peptide loading were used as control. After the last immunization, a wash was performed to remove the free peptide and both types of splenocytes were mixed in equal proportions and injected into the vaccinated animals. After 16 hours the inguinal lymph nodes of the vaccinated mice were removed and the two fluorescence intensities were measured by flow cytometry. The percentage of specific lysis was calculated according to the formula: 100−[(CFSEhigh/CFSElow)×100]. The OVA/VSSP GM3 (18:1) vaccine (FIG. 2), induces 60% of specific lysis, a value nearly three times higher than the one achieved with the OVA/VSSP GM3 (natural source) and OVA/VSSP GM3 (18:0) vaccines.

Figure 3:
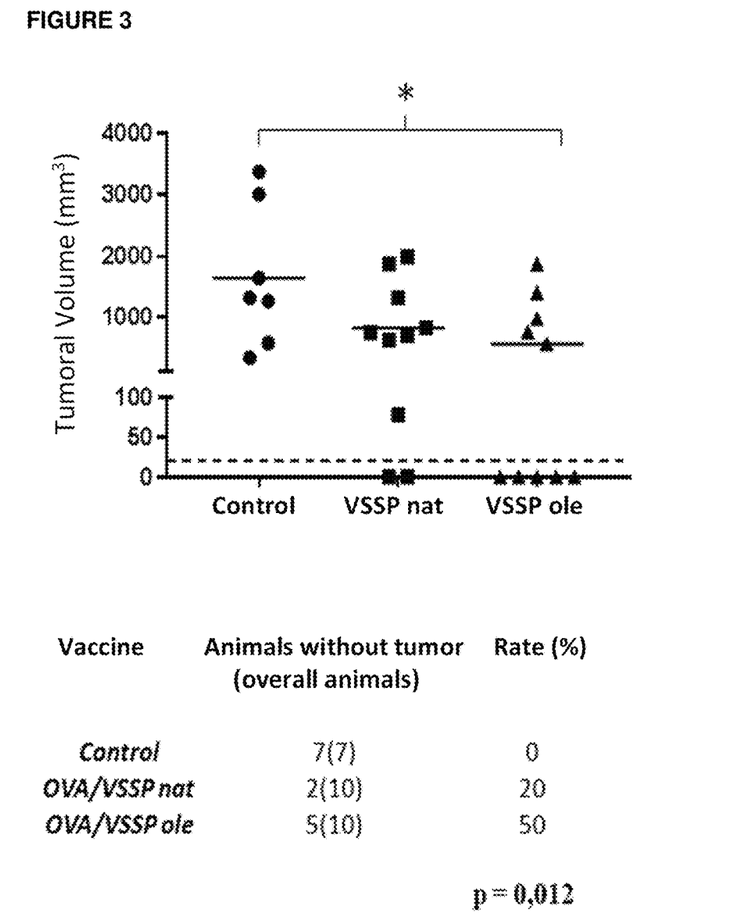
FIG. 3. Anti-tumor effect in the EG7 model of treatment with OVA vaccines employing VSSP nanoparticles as adjuvants containing different GM3 molecular species. The graph shows the individual values of tumor volume of each group and its average, on day 20 of the experiment. The dotted line represents the value below which the tumors were classified as not in progression. On the right, the frequency of animals in each group that did not have tumor progression with the treatments is shown.

Example 3. The Use of Nanoparticles of VSSP Containing GM3 (18:1) as Adjuvant in Therapeutic Cancer Vaccines Improve its Antitumor Effect, Compared to Nanoparticles Including GM3 Obtained from Natural Sources Three groups of female C57BL/6 mice (10 animals per group) were SC inoculated on day 0 with $3 \times 10^5$ cells of EG.7 tumor (a variant of EL4 thymoma genetically modified to express OVA as neo antigen). Subsequently, on days 4, 5 and 11, three successive immunizations by SC route were performed with two different vaccine formulations of OVA: the first (200 μg/dose) was adjuvated in VSSP GM3 (natural source) and the second in VSSP GM3 (18:1) (200 μg/dose). The third group of mice was injected with phosphate buffer with the same scheme and used as control of the experiment. Seven days after the tumor was inoculated, the tumor volume (TV) was measured twice a week. The animals were sacrificed when the tumor showed necrosis or when the tumor size exceeded 17 mm in diameter. On day 20 of the experiment (FIG. 3) superiority of the OVA/VSSP GM3 (18:1) therapeutic vaccine with respect to the OVA/VSSP GM3 (natural source) formulation was observed (TV means: VSSP GM3 (18:1) 560 mm³; natural 740 mm³; control 1640 mm³) (p=0.037 ANOVA and Tukey tests). More importantly, it was found that in the group treated with the OVA/VSSP GM3 (18:1) preparation, 50% of the animals did not show tumor progression in spite of EG7 being an aggressive model (100% of animals with progression was observed in the control group). In animals vaccinated with OVA/VSSP GM3 (natural source), only 20% showed no progression (p=0.012, Chi square test).

Example 4. Induction of High Titers of HER3 Specific Abs by the HER3/VSSP GM3 Vaccine Preparation (18:0)

BALB/c mice (n=5) were SC immunized with a vaccine preparation containing 200 µg of HER3 ECD mixed with 200 µg of GM3 VSSP (18:0). Immunizations were carried out on days 0, 14, 28 and 42. Blood was extracted to process the serum on day 35 (1 st extraction) and on day 56 (2nd extraction) and specific Abs titers against the the HER3 ECD were determined by ELISA. The plates were coated with 10 µg/mL of HER3 ECD and incubated at 37° C. After blocking, serum dilutions (1/100, 1/1000, 1/5000, 1/10000) were added. The reaction was visualized using an anti-murine IgG Ab/peroxidase conjugate (Sigma) and the corresponding substrate.

Figure 4:
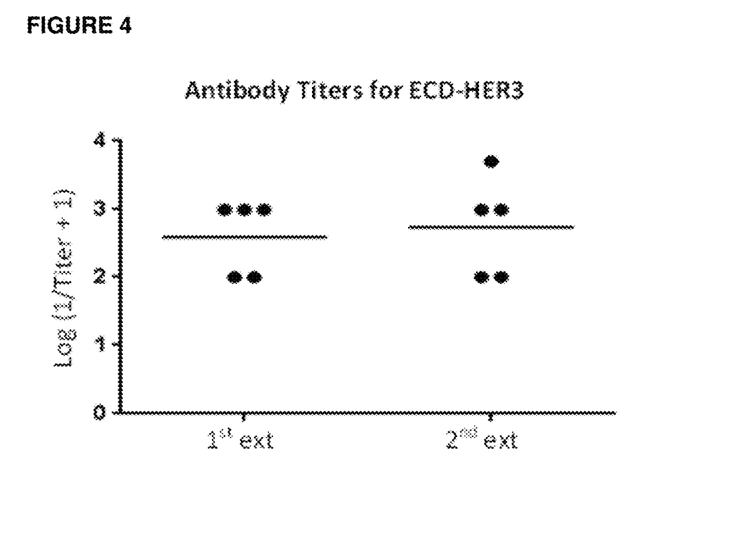
FIG. 4. IgG titers induced by the HER3 vaccine preparation adjuvated in VSSP GM3 (18:0), as measured by ELISA.

Immunized mice developed specific IgGs, with titers up to 1/5000 (FIG. 4). This result demonstrates the potential of GM3 VSSP (18:0) to activate the humoral immune response against very poorly immunogenic antigens such as autologous tumor antigens.

Example 5. Comparison of the Induction of Specific IgGs by the Bivalent HER1+HER2 Vaccine Either Adjuvated in VSSP GM3 (18:0) or in VSSP GM3 (Natural Source)

BALB/c mice (n=5) were immunized with the vaccine preparations containing the mixture of 100 µg of HER1 ECD and 100 µg of HER2 ECD adjuvated in 200 µg of VSSP GM3 (natural source) (Group 1) or 200 µg of VSSP GM3 (18:0) (Group 2). The immunizations were carried out by SC route on days 0, 14 and 28. Blood extraction and process were on day 35. The specific Abs titers against HER1 and HER2 ECD were determined by ELISA. For this the plates were coated with 5 µg/mL of HER1 ECD or 5 µg/mL of HER2 ECD and incubated at 37° C. After blocking, serum dilutions were added (1/100, 1/1000, 1/10 000, 1/50 000, 1/100 000). The reaction was visualized using an anti-murine IgG Ab/alkaline phosphatase conjugate and the corresponding substrate. Pre-immune serum was used as a negative control.

Figure 5A:
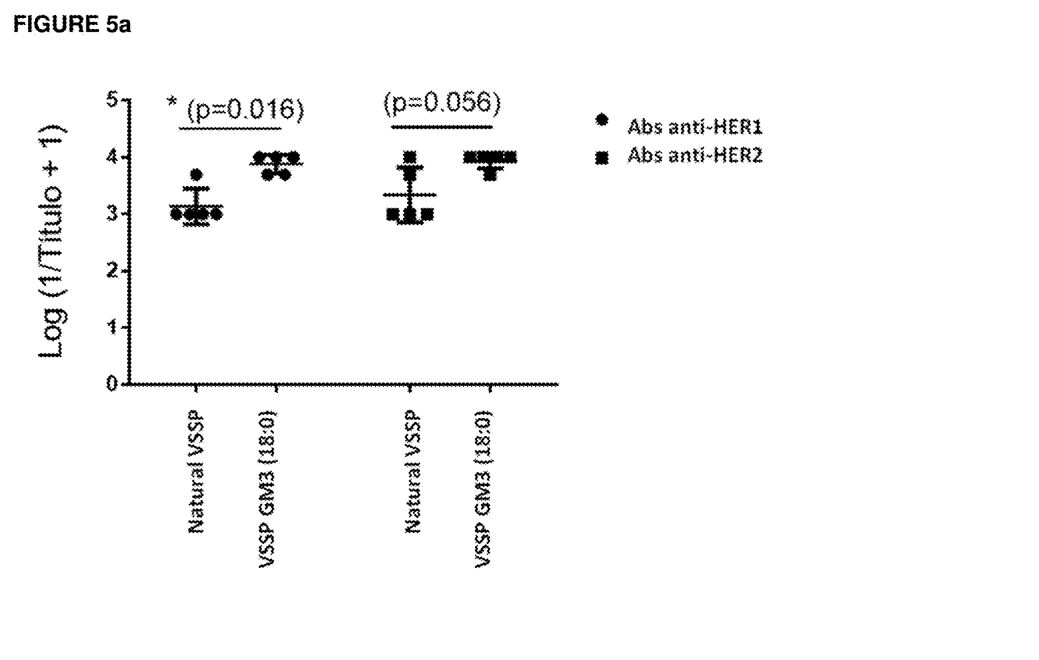
FIG. 5a. Comparison of specific Abs titers against HER1 and HER2 induced by the HER1+HER2 bivalent vaccine preparation adjuvated in VSSP GM3 (18:0) against the one adjuvated in VSSP GM3 (natural source), as measured by ELISA.
Figure 5B:
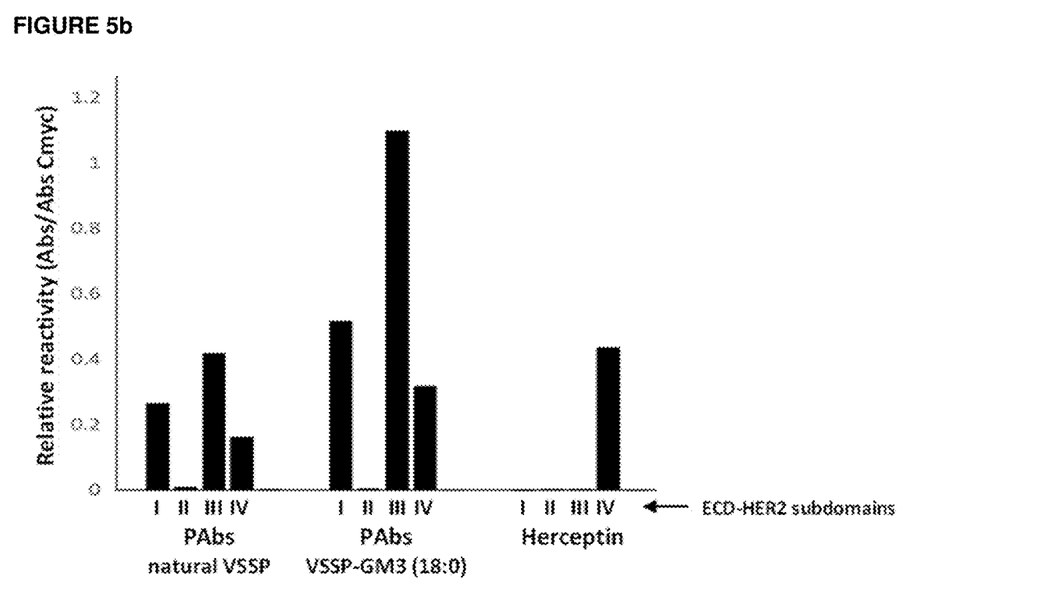
FIG. 5b. Comparison measured by ELISA of titers of specific Abs against the DEC-HER2 subdomains induced by the bivalent HER1+HER2 vaccine preparation adjuvated in GM3 VSSP (18:0) against the one adjuvated in VSSP GM3 (natural source).

All immunized mice developed specific IgG Abs. The Abs titers specific for the HER1 ECD were higher in Group 2, the group in which the adjuvant used was GM3 VSSP (18:0), as compared with the Abs titers raised in Group 1, which used VSSP GM3 (natural source) as adjuvant (FIG. 5a). On the other hand, even if in terms of specific Abs raised against the HER2 ECD there were no significant differences between the Abs titers induced in Groups 1 and 2, there was a tendency to an increase in the titers in Group 2, the group in which the vaccine preparation had the GM3 VSSP (18:0) as adjuvant. Given the trend observed in the recognition of HER2 ECD, a titration against the HER2 ECD subdomains (subdomains I, II, III and IV, expressed on filamentous phages) with the purified polyclonal antibodies (PcAb) isolated from the immune sera was performed. To this purpose, the ELISA plates were coated with 10 µg/mL of the PcAb and incubated at 37° C. Then the phage samples expressing the different subdomains of HER2 were added and the colorimetric signal was detected with the anti-phage antibody conjugated to peroxidase (GE-Healthcare). PcAb from animals in which the GM3 VSSP (18:0) was used as an adjuvant, showed more reactivity against the HER2 ECD subdomains I, III and IV than the antibodies purified from animals in which the VSSP GM3 (natural source) was employed (FIG. 5b).

Figure 6:
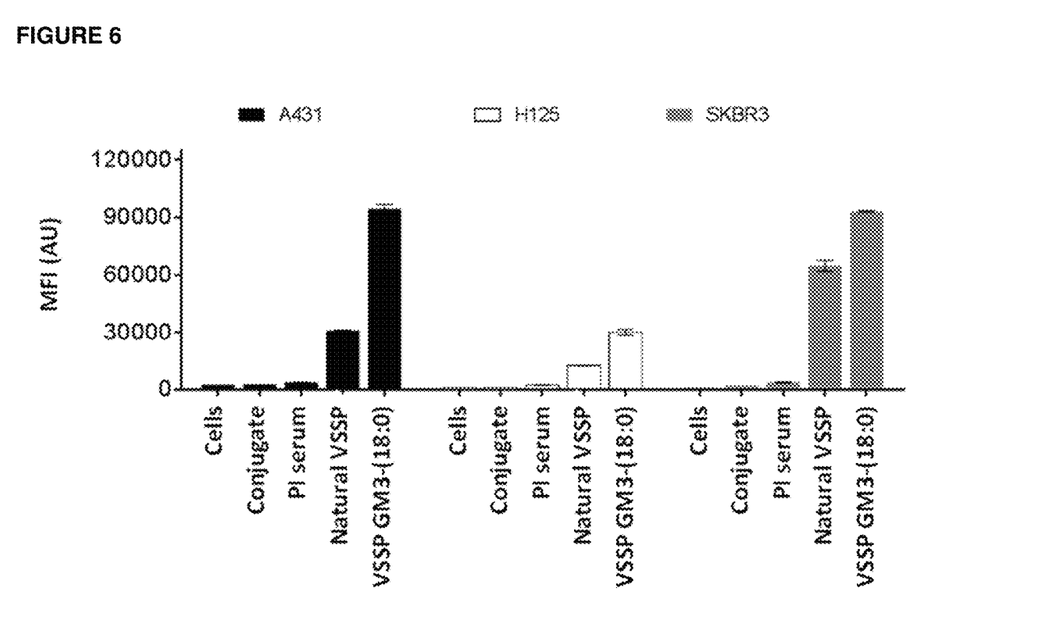
FIG. 6. Comparison measured by flow cytometry of the recognition of tumor lines HER1+/HER2+ by Abs induced with the bivalent vaccine preparation HER1+HER2 adjuvated in GM3 VSSP (18:0) against the one adjuvated in VSSP GM3 (natural source).

Example 6. Higher Recognition of HER1+/HER2+ Tumor Cell Lines by Abs Induced with the HER1+HER2 Bivalent Vaccine Adjuvated in VSSP GM3 (18:0) as Compared to the Vaccine Using the VSSP GM3 (Natural Source) as Adjuvant BALB/c mice (n=5) were SC immunized with vaccine preparations containing the mixture of 100 µg of HER1 ECD and 100 µg of HER2 ECD adjuvated in 200 µg of VSSP GM3 (natural source) or adjuvated in 200 µg of VSSP GM3 (18:0). Immunizations were performed on days 0, 14 and 28 and sera corresponding to day 35 was used to evaluate the recognition of tumor cell lines expressing HER1 and HER2 (A431 epithelial carcinoma of the vulva (ATCC-CRL 1555), H125 non-small cell lung carcinoma (ATCC-CRC 5801) and SKBR3 breast carcinoma (ATCC-HTB 30) by flow cytometry. To perform the measurement, $10^5$ cells from each cell line were blocked with 2% fetal calf serum in phosphate buffered saline and subsequently incubated with a 1/200 dilution of a mixture of sera from each treated group. The binding of the specific Abs to the HER1 and HER2 receptors in the tumor cells was visualized using an anti-murine IgG Ab/FITC (Sigma) conjugate and by acquiring at least 5000 cells in the flow cytometer. A mixture of pre-immune sera was used as a negative control in each group evaluated. Sera induced by the vaccine preparation adjuvated in VSSP GM3 (18:0) recognized with higher intensity the evaluated tumor cells lines (FIG. 6).

Example 7. The Bivalent HER1+HER2 Vaccine Adjuvated in GM3 VSSP (18:0) Induce Antibodies with Increased Impact on the Viability of the H125 Tumor Cell Line as Compared to the Composition Using VSSP GM3 (Natural Origin)

Figure 7:
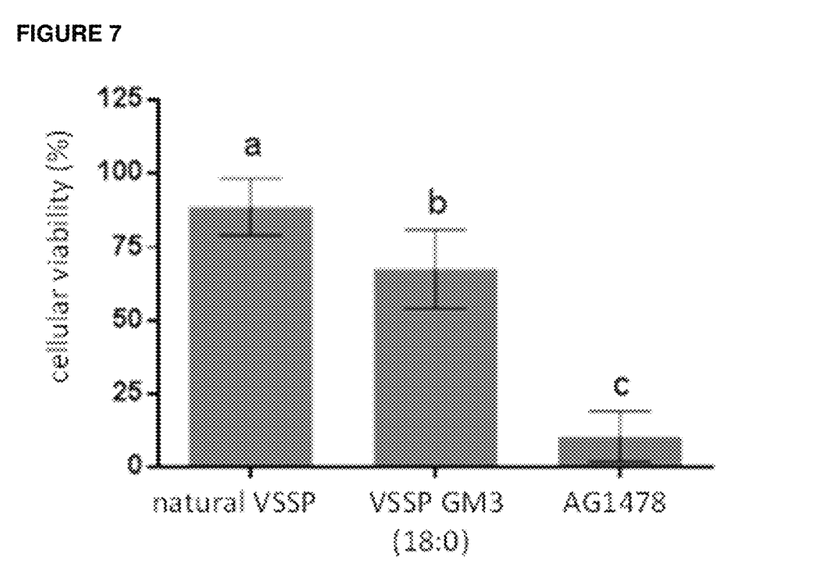
FIG. 7. Comparison as measured by MTT colorimetric assay of the effect on the viability of the H125 HER1+/HER2+ tumor line of the Abs induced by the bivalent HER1+HER2 vaccine preparation adjuvated in GM3 VSSP (18:0) against the one adjuvated in VSSP GM3 (natural source).

H125 cells ($10^5$) were incubated for 72 hours with mixtures of sera obtained from BALB/c mice immunized with three doses every fifteen days of the bivalent vaccine preparations containing the mixture of 100 µg of HER1 ECD and 100 µg of HER2 ECD, adjuvated in GM3 VSSP (18:0) or in VSSP GM3 (natural origin) at 1/20 dilution. As a negative control a mixture of pre-immune sera was used at the same dilution, while as a positive control 10 µM of AG1478 tyrosine kinase inhibitor was employed. The determination of the effect of immune sera on cell viability was performed using MTT colorimetric assay, and the absorbance reading was performed at 540 nm and 630 nm. Cell viability was determined by the formula:

$$\text{Cell viability } (\%) = \frac{(A540 \text{ nm} - A630 \text{ nm}) \text{ } inmune \text{ serum}}{(A540 \text{ nm} - A630 \text{ nm}) \text{ pre-}inmune \text{ serum}} \times 100$$

Sera induced by the vaccine adjuvated in GM3 VSSP (18:0) significantly decreased the cell viability as compared to the composition using VSSP GM3 (natural origin). (FIG. 7)

Example 8. The HER1 Vaccine Adjuvated in GM3 VSSP (18:0) Induce Abs with More Reactivity Against HER1+Tumor Cell Lines, Compared to the Preparation Using VSSP GM3 (Natural Origin)

Figure 8:
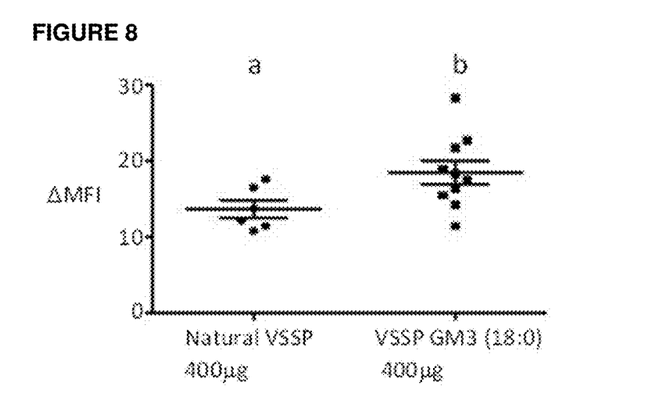
FIG. 8. Comparison as measured by flow cytometry of the recognition of the tumor line MDA-MB468 (HER1+) by the Abs induced with the HER1 vaccine preparation adjuvated in GM3 VSSP (18:0) against the one adjuvated in VSSP GM3 (natural source).

C57BL/6 mice (n=5) were SC immunized with vaccine preparations containing 200 μg of HER1 ECD adjuvated in 400 μg of VSSP GM3 (natural origin) or in 400 μg of GM3 VSSP (18:0). Immunizations were performed on days 0, 14, 28 and 42, whereas at day 56 animals were bleed in order to evaluate sera reactivity against the intensive HER1 expressing MDA-MB468 breast carcinoma cell line (ATCC-HTB 132) by flow cytometry. Basically, $10^5$ cells were blocked with 2% fetal calf serum in phosphate buffer saline and subsequently incubated with a 1/100 dilution of the mixture of the sera from each treated group. The specific Abs binding to the HER1 receptors at the tumor cells was visualized by means of an anti-murine IgG Ab/FITC (Sigma) conjugate and by acquiring at least 5000 cells in the flow cytometer. As a negative control, a mixture of pre-immune sera in each group evaluated was used. Sera induced by the vaccine adjuvated in VSSP GM3 (18:0) reacted more intensively with the tumor cells, as compared to the composition using VSSP GM3 (natural origin) (FIG. 8).

Example 9. The HER1 Vaccine Adjuvated in VSSP GM3 (18:0) Induce Abs with Increased Capability to Inhibit the Activation of HER1 as Compared to the Composition Using VSSP GM3 (Natural Origin)

Four groups of C57BL/6 mice (n=5) were SC immunized with one of the following vaccine preparations:
Group 1: 200 μg of HER1-ECD adjuvated in 200 μg of VSSP GM3 (natural origin)
Group 2: 200 μg of HER1-ECD adjuvated in 200 μg of GM3 VSSP (18:0)
Group 3: 200 μg of HER1-ECD adjuvated in 400 μg of VSSP GM3 (natural origin)
Group 4: 200 μg of HER1-ECD adjuvated in 400 μg of GM3 VSSP (18:0)

Figure 9:
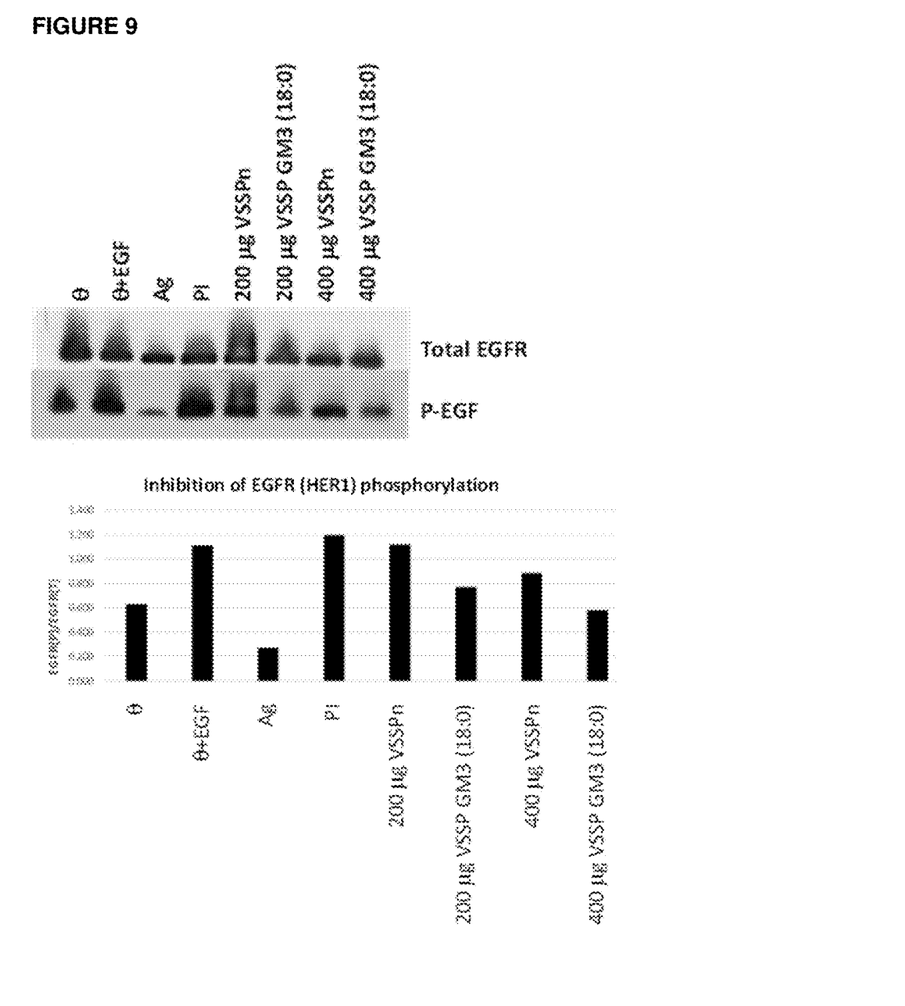
FIG. 9. Comparison as measured by Western Blot of the inhibition of HER1 activation by the Abs induced with the HER1 vaccine preparation adjuvated either in VSSP GM3 (18:0) or in VSSP GM3 (natural source).

Immunizations were carried out on days 0, 14, 28, 42 and sera corresponding to day 56 were used to evaluate the capacity of the generated Abs to inhibit HER1 phosphorylation in the presence of EGF. Briefly, H292 lung carcinoma cells (CRL 1848) were incubated for 2 hours with a mixture of sera at a 1/100 dilution. Subsequently, the cells were stimulated with 100 ng/ml of EGF for 10 minutes to induce the activation of HER1. The effect of the sera on the phosphorylation of HER1 was measured by Western Blot, using specific Abs for the detection of phosphorylated HER1 and β-actin. Cells treated with EGF were used as control of HER1 activation. A mixture of pre-immune sera at a 1/100 dilution was used as a negative control of HER1 inhibition, and 10 μM of AG1478 tyrosine kinase inhibitor was used as a positive inhibition control. A photograph of the experiment was submitted to densitometry analysis for data normalization. Sera obtained from animals immunized with the vaccines using GM3 VSSP (18:0) as adjuvant exhibited a stronger inhibition of the HER1 receptor activation in terms of phosphorylation than sera coming from the groups of mice injected with the composition using VSSP GM3 (natural source) at 200 μg and 400 μg dose as well (FIG. 9). This result demonstrates the superiority of the vaccine containing GM3 VSSP (18:0) as adjuvant in terms of the quality of the induced humoral immune response.

Example 10. Effect of the PyrGnRHm1-TT/VSSP GM3 (18:0) Vaccine Formulation on the Prostate of Copenhagen Rats Male Copenhagen rats of 8-12 weeks of age were used. The animals were divided into 3 groups of 10 animals each.
Group 1: Injected with Placebo (Montanide ISA 51 VG/VSSP GM3 (18:0)
Group 2: Immunized with PyrGnRHm1-TT/Montanide ISA 51 VG
Group 3: Immunized with PyrGnRHm1-TT/Montanide ISA 51 VG/VSSP GM3 (18:0)

For the preparation of the immunogen, the PyrGnRHm1-TT peptide was dispersed in distilled water and VSSP nanoparticles until it reached a final concentration of 750 μg of peptide and 120 μg of VSSP in 250 μL. Then this mixture was proportionally formulated 50:50 (v/v) with Montanide ISA 51 VG. The rats received 4 immunizations with a fortnightly frequency.

Figure 10:
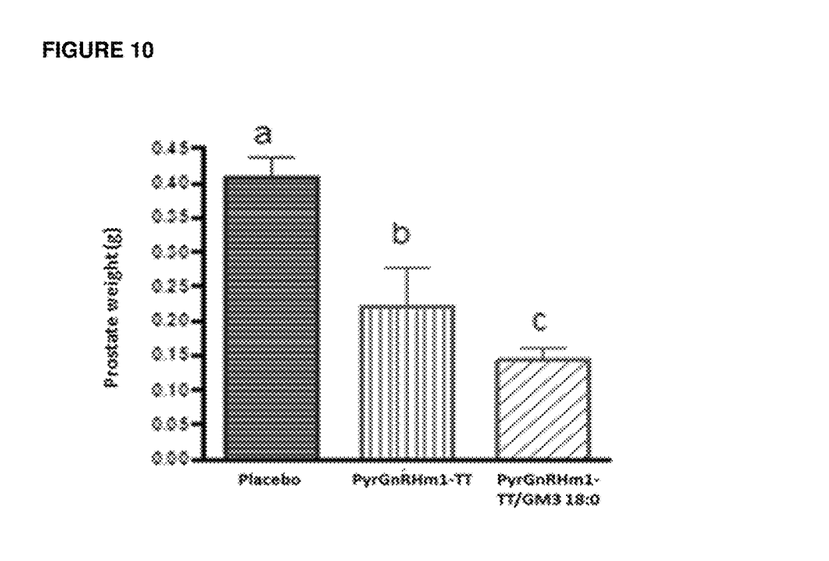
FIG. 10. Effect of immunization with PyrGnRHm1-TT peptide with and without VSSP GM3 (18:0) on the weight of Copenhagen rat prostate.

The immunization with the PyrGnRHm1-TT peptide emulsified in Montanide ISA 51 VG, produced a significant decrease in the size of the prostate, as compared to immunization with placebo ($p<0.05$). This difference, however, was much greater when the peptide PyrGnRHm1-TT was emulsified in the presence of VSSP GM3 (18:0) ($p<0.01$) (FIG. 10)

Example 11. Induction of Antitumor Responses in the R3327-H Dunning Model Using the PyrGnRHm1-TT Peptide Adult Copenhagen rats were SC transplanted in the distal zone of the right hind limb with (2×2×2 mm) tumor fragments of the Dunning R3327-H murine tumor model. The animals were divided into four groups that received different treatments:
Group 1: Placebo: Montanide ISA 51 VG/VSSP GM3 (18:0)
Group 2: Castrated
Group 3: Immunized with the PyrGnRHm1-TT peptide/Montanide ISA 51 VG
Group 4: Immunized with the PyrGnRHm1-TT peptide/Montanide ISA 51 VG/VSSP GM3 (18:0)

Figure 11:
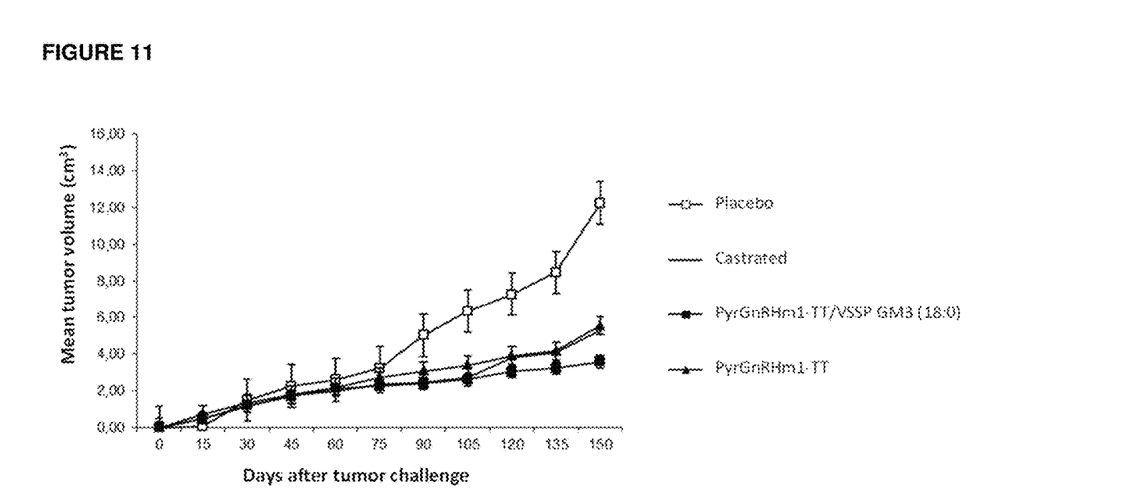
FIG. 11. Evaluation of the tumor growth rate in Copenhagen rats implanted with the Dunning R3327-H tumor line.

Immunizations with the corresponding vaccines started when tumors reached a diameter of approximately 10 mm. A total of 7 immunizations were administered every 15 days. While a pronounced growth of the tumor in the placebo group (Group 1) was observed (FIG. 11), the castrated and immunized groups (Groups 2, 3 and 4) showed a marked inhibition of tumor growth ($p<0.01$). This effect was more significant in rats immunized with the PyrGnRHm1-TT peptide emulsified in the presence of VSSP GM3 (18:0) ($p=0.005$).

We claim:

1. A method of stimulating an antigen-specific cellular immune response in a subject, the method comprising administering to the subject an adjuvant comprising nanoparticles comprising GM3 ganglioside and hydrophobic proteins of the outer membrane complex of the bacterium *Neisseria meningitidis*,
    wherein the fatty acid in the ceramide of the GM3 ganglioside consists of oleic acid (18:1), and
    wherein the GM3 ganglioside and hydrophobic proteins of the outer membrane complex of the bacterium *Neisseria meningitides* are in association with each other.

2. The method of claim 1, wherein the method comprises administering a vaccine composition comprising the adjuvant and an antigen to the subject.

3. The method of claim 2, wherein the vaccine composition further comprises a second adjuvant selected from alum and an oily adjuvant.

4. The method of claim 2, wherein the antigen is the extracellular domains of a growth factor receptor, or portion thereof.

5. The method of claim 4, wherein the growth factor receptors are HER1, HER2, and/or HER3, alone or in combination.

6. The method of claim 2, wherein the antigen is the PyrGnRHm1-TT peptide.

7. The method of claim 1, wherein the subject has cancer.

8. The method of claim 7, wherein the cancer is lung cancer, hepatocellular cancer, gastric cancer, pancreatic cancer, head and neck cancer, glioblastoma, cervical cancer, ovarian cancer, bladder cancer, breast cancer, colorectal cancer, prostate cancer, salivary gland carcinoma, kidney cancer, vulva and thyroid tumors, anal carcinoma, or penile carcinoma.

9. The method of claim 1, wherein the subject has a chronic infection caused by an oncogenic virus.

10. The method of claim 2, wherein the vaccine composition is administered via subcutaneous, intradermal, intramuscular, intranodal, or intratumoral routes or by direct application to mucous membranes.

11. The method of claim 2, wherein the vaccine composition is administered every 15 days for at least a total of five induction doses and subsequently in monthly maintenance doses for at least six months.

12. A method of stimulating an antigen-specific humoral immune response in a subject, the method comprising administering to the subject an adjuvant comprising nanoparticles comprising GM3 ganglioside and hydrophobic proteins of the outer membrane complex of the bacterium *Neisseria meningitidis*,
    wherein the fatty acid in the ceramide of the GM3 ganglioside consists of stearic acid (18:0), and
    wherein the GM3 ganglioside and hydrophobic proteins of the outer membrane complex of the bacterium *Neisseria meningitides* are in association with each other.

13. The method of claim 12, wherein the method comprises administering a vaccine composition comprising the adjuvant and an antigen to the subject.

14. The method of claim 13, wherein the vaccine composition further comprises a second adjuvant selected from alum and an oily adjuvant.

15. The method of claim 13, wherein the antigen is the extracellular domains of a growth factor receptor, or portion thereof.

16. The method of claim 15, wherein the growth factor receptor is HER1, HER2, and/or HER3 alone or in combination.

17. The method of claim 13, wherein the antigen is the PyrGnRHm1-TT peptide.

18. The method of claim 12, wherein the subject has cancer.

19. The method of claim 18, wherein the cancer is lung cancer, hepatocellular cancer, gastric cancer, pancreatic cancer, head and neck cancer, glioblastoma, cervical cancer, ovarian cancer, bladder cancer, breast cancer, colorectal cancer, prostate cancer, salivary gland carcinoma, kidney cancer, vulva and thyroid tumors, anal carcinoma, or penile carcinoma.

20. The method of claim 12, wherein the subject has a chronic infection caused by an oncogenic virus.

21. The method of claim 13, wherein the vaccine composition is administered via subcutaneous, intradermal, intramuscular, intranodal, or intratumoral routes or by direct application to mucous membranes.

22. The method of claim 13, wherein the vaccine composition is administered every 15 days for at least a total of five induction doses and subsequently in monthly maintenance doses for at least six months.

23. The method of claim 12, wherein the method further comprises administering to the subject an additional adjuvant comprising nanoparticles comprising GM3 ganglioside and hydrophobic proteins of the outer membrane complex of the bacterium *Neisseria meningitidis,*
   wherein the fatty acid in the ceramide of the GM3 ganglioside consists of oleic acid (18:1), and
   wherein the GM3 ganglioside and hydrophobic proteins of the outer membrane complex of the bacterium *Neisseria meningitides* are in association with each other.

24. A method comprising administering an adjuvant comprising nanoparticles comprising GM3 ganglioside and hydrophobic proteins of the outer membrane complex of the bacterium *Neisseria meningitidis* to a subject,
   wherein the fatty acid in the ceramide of the GM3 ganglioside consists of oleic acid (18:1), and
   wherein the GM3 ganglioside and hydrophobic proteins of the outer membrane complex of the bacterium *Neisseria meningitides* are in association with each other.

* * * * *

SEQUENCE LISTING

```
Sequence total quantity: 3
SEQ ID NO: 1            moltype = AA  length = 10
FEATURE                 Location/Qualifiers
source                  1..10
                        mol_type = protein
                        organism = Branchiostoma lanceolatum
SEQUENCE: 1
EHWSYGLRPG                                                              10

SEQ ID NO: 2            moltype = AA  length = 10
FEATURE                 Location/Qualifiers
REGION                  1..10
                        note = Description of Artificial Sequence: GnRH G/P mutation
source                  1..10
                        mol_type = protein
                        organism = synthetic construct
SEQUENCE: 2
EHWSYPLRPG                                                              10

SEQ ID NO: 3            moltype = AA  length = 15
FEATURE                 Location/Qualifiers
source                  1..15
                        mol_type = protein
                        organism = Clostridium tetani
SEQUENCE: 3
QYIKANSKFI GITEL                                                        15
```